(12) United States Patent
Ghosh et al.

(10) Patent No.: US 9,283,209 B2
(45) Date of Patent: Mar. 15, 2016

(54) ORAL FORMULATIONS OF DEFERASIROX

(71) Applicants: Indrajit Ghosh, Hillsborough, NJ (US); Jia-Ai Zhang, Skillman, NJ (US)

(72) Inventors: Indrajit Ghosh, Hillsborough, NJ (US); Jia-Ai Zhang, Skillman, NJ (US)

(73) Assignee: NOVARTIS AG, Basel (CH)

( * ) Notice: Subject to any disclaimer, the term of this patent is extended or adjusted under 35 U.S.C. 154(b) by 260 days.

(21) Appl. No.: 14/198,872

(22) Filed: Mar. 6, 2014

(65) Prior Publication Data
US 2015/0017241 A1 Jan. 15, 2015

Related U.S. Application Data

(60) Provisional application No. 61/774,893, filed on Mar. 8, 2013, provisional application No. 61/824,435, filed on May 17, 2013.

(51) Int. Cl.
| | | |
|---|---|---|
| A61K 31/41 | (2006.01) | |
| A61K 9/22 | (2006.01) | |
| A61K 31/4196 | (2006.01) | |
| A61K 9/20 | (2006.01) | |
| A61K 9/28 | (2006.01) | |
| A61K 9/50 | (2006.01) | |

(52) U.S. Cl.
CPC .......... *A61K 31/4196* (2013.01); *A61K 9/2031* (2013.01); *A61K 9/2054* (2013.01); *A61K 9/2077* (2013.01); *A61K 9/2095* (2013.01); *A61K 9/2846* (2013.01); *A61K 9/2886* (2013.01); *A61K 9/2893* (2013.01); *A61K 9/5026* (2013.01); *A61K 9/5089* (2013.01)

(58) Field of Classification Search
USPC ......................................... 514/383; 424/468
See application file for complete search history.

(56) References Cited

FOREIGN PATENT DOCUMENTS

| WO | WO97/49395 A1 | 12/1997 |
|---|---|---|
| WO | WO2005/097062 A1 | 10/2005 |
| WO | WO2009130604 A2 | 10/2009 |
| WO | WO2010/143006 A1 | 12/2010 |

*Primary Examiner* — Adam C Milligan
(74) *Attorney, Agent, or Firm* — Eckert Seamans Cherin & Mellott, LLC

(57) ABSTRACT

Orally administerable deferasirox formulations are disclosed having reduced release under gastric conditions and fast release at near neutral pH or at neutral pH.

3 Claims, 13 Drawing Sheets

Dissolution profile of deferasirox capsules consisting of enteric coated pellets prepared by extrusion spheronization.

ORAL FORMULATIONS OF DEFERASIROX

FIELD OF THE INVENTION

Compositions and technologies of manufacturing medicaments for Exjade™ (desferasirox) with high drug loading to potentially reduce variability of the gastric emptying, minimize food effect, prevent gastric irritation and also reduce the size and delivery route of the dosage form to improve patient compliance.

BACKGROUND OF THE INVENTION

Exjade™ (deferasirox) is a marketed product from Novartis that is formulated as dispersible tablets in 125 mg, 250 mg and 500 mg dose strengths. Exjade™ (deferasirox) is given once daily for the treatment of chronic iron overload due to blood transfusions, which is referred to by medical professionals and clinicians as transfusional hemosiderosis, in patients 2 years of age and older.

Due to the poor solubility of Exjade™ (deferasirox), a high dose is required to achieve the desired therapeutic effect, which results in unwanted side effects, such as gastrointestinal (GI) irritation and kidney toxicity. The poor solubility of Exjade™ (deferasirox) also presents technical difficulties in developing pharmaceutical formulations, as seen from the solubility profile summarized in Table 1. To meet the high dose requirement and reduce pill burden Exjade™ (deferasirox) was developed as dispersible tablets with about 29.4% drug load. The disadvantage of this type of formulation is that the tablets have to be dispersed in water or appropriate liquid, such as in orange juice or apple juice and stirred until a fine suspension is obtained prior to administration. Further, the dispersible tablets have to be taken at least 30 minutes before food.

TABLE 1

| Exjade ™ (deferasirox) Solubility Profile | |
|---|---|
| pH | Solubility (mg/ml) at 37 C. |
| water | 0.02 |
| 1 | <0.01 |
| 2 | <0.01 |
| 3 | <0.01 |
| 4 | <0.01 |
| 5 | <0.01 |
| 7.5 | 0.167 |

Gastrointestinal (GI) irritation has been reported for patients using the current dispersible tablets. Upper gastrointestinal ulceration and hemorrhage has also been reported in patients, including children and adolescents. Multiple ulcers have been observed in some patients. Stomach bleeding is a severe side effect that occurs for patients currently under Exjade therapy because of acidity of Exjade™ (deferasirox), and local accumulation of drug content. Therefore, it is desirable to re-formulate an Exjade™ (deferasirox) dispersible formulation to limit the direct contact of drug compound with stomach mucosa. It is further desirable to provide a high load deferasirox formulation that has no food effect. For instance, as enteric coated form or multi-particulate form where dosage form is emptied faster from the stomach. In addition, data from THALASSA (NTDT) study placebo arms (contains all components in Exjade™ dispersible tablets (except API) suggest that excipients in the marketed dispersible formulation could contribute to GI adverse effects (AE) profile of Exjade™.

The current invention describes formulated compositions and the corresponding technology of manufacturing tablets for Exjade™ (deferasirox) to prevent gastrointestinal irritation, having no food effect and improve patient compliance.

With aforementioned cumbersome in drug administration, it is also desirable to re-formulate the current dispersible Exjade™ (deferasirox) tablets into swallowable (ingestable, orally administerable) tablets and sachets, which increase the drug load by up to and greater than 100% of the current dispersible tablet and sachet per dose requiring less pill burden while maintaining equivalent pharmacokinetic profile, and consequently the therapeutic outcome as compared to commercially marketed dispersible Exjade™ (deferasirox) tablets.

SUMMARY OF THE INVENTION

An aspect of the present invention provides a tablet for treating diseases which cause an excess of metal, such as iron, in a human or animal body or are caused by an excess of metal in a human comprising Exjade™ (deferasirox) of the formula I:

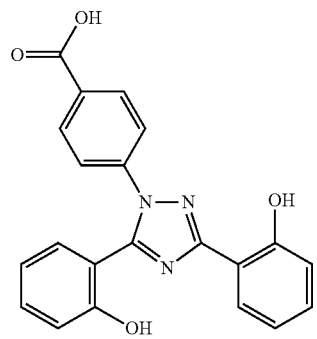 [SMILES: O=C(O)c1ccc(-n2nc(-c3ccccc3O)nc2-c2ccccc2O)cc1]

or a pharmaceutically acceptable salt thereof present in an amount of from 45% to 60% by weight based on the total weight of the tablet, said tablet having a reduced release under gastric conditions and fast release at near neutral pH or at neutral pH.

Typically, a drug product that shows faster dissolution will have a much higher exposure level when tested in humans. Surprisingly, in the current case. Exjade™ (deferasirox) tablets formulated to have slower release showed much higher bioavailability and no food effects when compared with commercial dispersible tablets, which have a faster dissolution rate but which exhibit significantly lower exposure levels. The characteristics of the new swallowable (ingestable, orally administerable) tablets and sachets, such as its disintegration time and dissolution are uniquely needed to reach the intended exposure levels.

Another aspect of the present invention provides a coated tablet comprising (a) deferasirox or a pharmaceutically acceptable salt thereof, and (b) at least one pharmaceutically acceptable excipient suitable for the preparation of tablets, wherein deferasirox or a pharmaceutically acceptable salt thereof is present in an amount of from 45% to 60% by weight based on the total weight of the tablet. The tablets are optionally enteric coated.

Another aspect of the present invention provides a sachet comprising (a) deferasirox or a pharmaceutically acceptable salt thereof, and (b) at least one pharmaceutically acceptable excipient suitable for the preparation of sachets, wherein deferasirox or a pharmaceutically acceptable salt thereof is present in an amount of from 45% to 60% by weight based on the total weight of the sachet.

Another aspect of the present invention provides a coated deferasirox tablet comprising:
(i) at least one filler in an amount of about to 10% to 40% by weight based on the total weight of the tablet;
(ii) at least one disintegrant in an amount of about 1% to 10% in weight based on the total weight of the tablet:
(iii) at least one binder in an amount of about 1% to 5% by weight based on the total weight of the tablet;
(iv) at least one surfactant in an amount of about 0.0% to 2% by weight based on the total weight of the tablet;
(v) at least one glidant in an amount of about 0.1% to 1% by weight based on the total weight of the tablet;
(vi) at least one lubricant in an amount of less than about 0.1% to 2% % by weight based on the total weight of the tablet; and
(vii) a coating.

Another aspect of the present invention provides a process for the preparation of a coated deferasirox tablet according to any one of the preceding claims, which process comprises
(i) mixing deferasirox or a pharmaceutically acceptable salt thereof and at least one pharmaceutically acceptable excipient;
(ii) wet-granulating the mixture obtained in step (i) in a high shear granulator followed by drying and screening to produce a granulate;
(iii) mixing the granulates obtained in step (ii) with at least one pharmaceutically acceptable excipient to form a mixture;
(iv) compressing the mixture obtained in step (iii) to form a tablet; and
(v) coating the tablet.

Yet another aspect of the present invention provides a process for the preparation of a coated deferasirox tablet, comprising the steps of:
(i) mixing deferasirox or a pharmaceutically acceptable salt and at least one pharmaceutically acceptable excipient;
(ii) wet-granulating the mixture obtained in step (i) in a high shear granulator;
(iii) extruding and spheronizing the wet granulates obtained in step (ii);
(iv) drying the extruded and spheronized pellets; and
(v) coating the pellets.

DETAILED DESCRIPTION OF THE INVENTION

Figure 1:
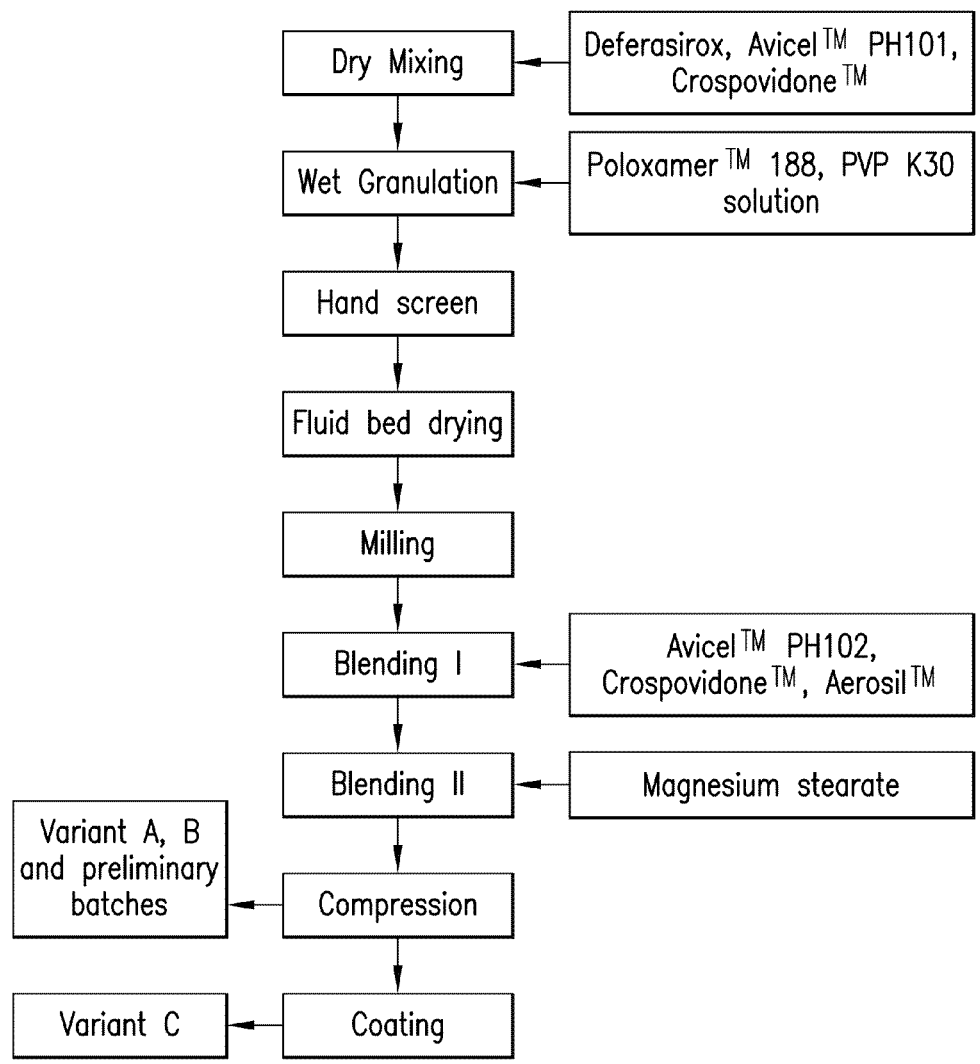
FIG. 1 depicts a flow chart showing the manufacturing process of coated deferasirox tablets prepared by wet granulation FIG. 2 summarizes the dissolution profile of deferasirox from tablets prepared by wet granulation FIG. 3 summarizes the dissolution profile of deferasirox from enteric coated tablets prepared by wet granulation.

The current commercial formulation of Exjade™ (deferasirox) is a dispersible tablet. The current formulation is dosed under fasted state due to a GI irritation issue. The new intended swallowable (ingestable, orally administerable) deferasirox tablets have an improved GI irritation AE profile due to a slower release profile and removal of sodium lauryl sulfate and lactose from the dispersible formulation. The invented formulation allows for patient compliance, no food effects and reduced GI irritation as compared to the current marketed Exjade™ (deferasirox) product.

The present invention provides a Exjade™ (deferasirox) formulation having a unique combination of excipients and a surfactant (e.g., a poloxamer) that are compatible with deferasiox at physiological pH environment. The invented formulation also possesses certain improved in vitro characteristics.

The invented process allows for and contributes to the high deferasirox loading. Wet granulation of the deferasirox active can be done with high drug loading (40-80% by weight) and compressed into tablets for enteric coating to achieve a final deferasirox loading of about 45-60% by weight, preferably 56% by weight.

A suitable dose of deferasirox ranges from 90 to 360 mg, especially, 90 mg, 180 mg, 360 mg unit dosage for film coated tablets and 100 to 400 mg. especially, 100 mg, 200 mg, 400 mg unit dosage for granule formulation filled into stickpacks. The dose of deferasirox administered to a patient depends on numerous factors such as weight of patient, the severity of symptom and the nature of any other drugs being administered. The current product of deferasirox is presented on the market with three dosage strengths, 125 mg, 250 mg and 500 mg. The present invention provides exemplary embodiments for manufacturing swallowable (ingestable, orally administerable) deferasirox tablets with different dissolution profiles that correspond to commercial Exjade™ (deferasirox) product From a human clinical study, the invented deferasirox formulation demonstrated higher bioavailability, as compared to the previous marketed Exjade™ (deferasirox) formulation. Therefore the therapeutic dose was adjusted accordingly to achieve comparable pharmacokinetic profile and similar therapeutic effect. In summary, the invented formulation was developed with higher deferasirox loading and superior bioavailability. Lowering the dose will eventually improve patient compliance.

In an exemplary embodiment, one or more pharmaceutically acceptable excipients are present in the deferasirox dispersible tablets, including but not limited to conventionally used excipients: at least one filler, e.g., lactose, ethylcellulose, microcrystalline cellulose; at least one disintegrant, e.g. cross-linked polyvinylpyrrolidinone. e.g. Crospovidone®; at least one binder, e.g. polyvinylpyridone, hydroxypropylmethyl cellulose; at least one surfactant, e.g. sodium laurylsulfate, poloxamer; at least one glidant, e.g. colloidal silicon dioxide; and at least one lubricant, e.g. magnesium stearate.

In one embodiment, the deferasirox granules and film-coated tablets will include the following compendial excipients: microcrystalline cellulose, povidone, crospovidone, poloxamer 188, colloidal silicon dioxide, and magnesium stearate. Opadry coating material (hypromellose, titanium dioxide, polyethylene glycol, Macrogol, talc and FD&C blue #2/Indigo carminine aluminum lake (C.I. 7305, E132)) is used for the film-coated tablets. Among the above excipients, only poloxamer 188 and the coating material represent new excipients for Exjade; lactose and sodium lauryl sulphate would no longer be present.

Reference is made to the extensive literature on the subject for these and other pharmaceutically acceptable excipients and procedures mentioned herein, see in particular Handbook of Pharmaceutical Excipients, Third Edition, edited by Arthur H. Kibbe, American Pharmaceutical Association, Washington, USA and Pharmaceutical Press, London; and Lexikon der Hilfsstoffe für Pharmazie, Kosmetik and angrenzende Gebiete edited by H. P. Fiedler, 4th Edition. Editor Cantor, Aulendorf and earlier editions.

Suitable fillers according to the invention include but are not limited to microcrystalline cellulose, including but not limited to Avicel™ PH 102, PH 101.

Suitable disintegrants according to the invention include but are not restricted to: maize starch, CMC-Ca, CMC-Na, microcrystalline cellulose, cross-linked polyvinylpyrrolidone (PVP), e.g. as known and commercially available under the trade names Crospovidone®, Polyplasdone®, available commercially from the ISP company, or Kollidon® XL, alginic acid, sodium alginate and guar gum. In one embodiment, cross-linked PVP. e.g. Crospovidone® is used.

Suitableinders include but are not restricted to: starches, e.g. potato, wheat or corn starch, microcrystalline cellulose, e.g. products such as Avice®, Filtrak®, Heweten® or Pharmacel®; hydroxypropyl cellulose, hydroxyethyl cellulose, hydroxypropylmethyl cellulose, e.g. hydroxypropylmethyl cellulose-Type 2910 USP, hypromellose, and polyvinylpyrrolidone, e.g. Povidone® K30 from BASF. In one embodiment, polyvinylpyrrolidone is used, most preferably PVP K30™.

Suitable surfactants according to the invention include but are not restricted to: sodium laurylsulfate, betain, quaternary ammonium salts, polysorbates, sorbitan erters and a poloxamer. In one embodiment, the surfactant is a poloxamer, preferably Pluronic™ F68 grade.

Suitable glidants include but are not restricted to: silica; colloidal silica, e.g. colloidal silica anhydrous, e.g. Aerosil® 200, magnesium trisilicate, powdered cellulose, starch and talc. Preferably, colloidal silicon dioxide is used.

Suitable lubricants include but are not restricted to: Mg-, Al- or Ca-stearate, PEG 4000-8000, talc, sodium benzoate, glyceryl mono fatty acid. e.g. having a molecular weight of from 200 to 800 Daltons, e.g. glyceryl monostearate (e.g. Danisco, UK), glyceryl dibehenate (e.g. Compritol ATO888™, Gattefossé France), glyceryl palmito-stearic ester (e.g. Precirol™, Gattefossé France), polyoxyethylene glycol (PEG, BASF), hydrogenated cotton seed oil (Lubitrab™, Edward Mendell Co inc), castor seed oil (Cutina™ HR, Henkel). In one embodiment, magnesium stearate is used.

Accordingly, in an exemplary embodiment, the present invention provides a tablet for treating diseases which cause an excess of metal, such as iron, in a human or animal body or are caused by an excess of metal in a human comprising Exjade™ (deferasirox) of the formula I:

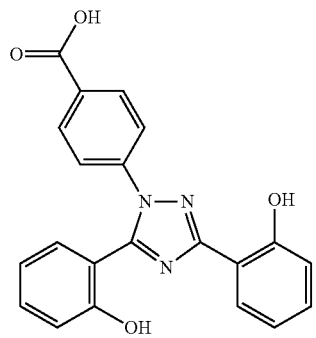

or a pharmaceutically acceptable salt thereof present in an amount of from 45% to 60% by weight based on the total weight of the tablet where said tablet having a reduced release under gastric conditions and fast release at near neutral pH or at neutral pH.

Typically, a drug product that shows faster dissolution will have a much higher exposure level when tested in humans. Surprisingly, in the current case, Exjade™ (deferasirox) tablets formulated to have slower release showed much higher bioavailability when compared with commercial dispersible tablets, which have a faster dissolution rate but which exhibit significantly lower exposure levels. The characteristics of the new swallowable (ingestable, orally administerable) tablets, such as its disintegration time and dissolution are uniquely needed to reach the intended exposure levels.

In a separate embodiment, the present invention provides a coated tablet comprising (a) deferasirox or a pharmaceutically acceptable salt thereof, and (b) at least one pharmaceutically acceptable excipient suitable for the preparation of tablets, wherein deferasirox or a pharmaceutically acceptable salt thereof is present in an amount of from 45% to 60% by weight based on the total weight of the tablet, wherein the tablets are optionally enteric coated.

In a separate embodiment, the present invention provides a coated deferasirox tablet comprising:
 (i) at least one filler in an amount of about to 10% to 40% by weight based on the total weight of the tablet;
 (ii) at least one disintegrant in an amount of about 1% to 10% in weight based on the total weight of the tablet;
 (iii) at least one binder in an amount of about 1% to 5% by weight based on the total weight of the tablet;
 (iv) at least one surfactant in an amount of about 0.0% to 2% by weight based on the total weight of the tablet;
 (v) at least one glidant in an amount of about 0.1% to 1% by weight based on the total weight of the tablet;
 (vi) at least one lubricant in an amount of less than about 0.1% to 2% % by weight based on the total weight of the tablet; and
 (vii) a coating, wherein the coating comprises a functional or non-functional polymer.

A. Manufacturing of Tablets by Wet Granulation Process

According to one embodiment, the present invention provides a process for the preparation of a coated deferasirox tablet according to any one of the preceding claims, which process comprises:
 (i) mixing deferasirox or a pharmaceutically acceptable salt thereof and at least one pharmaceutically acceptable excipient;

(ii) wet-granulating the mixture obtained in step (i) in a high shear granulator followed by drying and screening to produce a granulate;
(iii) mixing the granulates obtained in step (ii) with at least one pharmaceutically acceptable excipient to form a mixture;
(iv) compressing the mixture obtained in step (iii) to form a tablet; and
(v) coating the tablet, wherein the coating further comprises a functional or non-functional polymer.

A flow chart showing the manufacturing process of coated deferasirox tablets prepared by wet granulation is summarized in FIG. 1.

Figure 2:
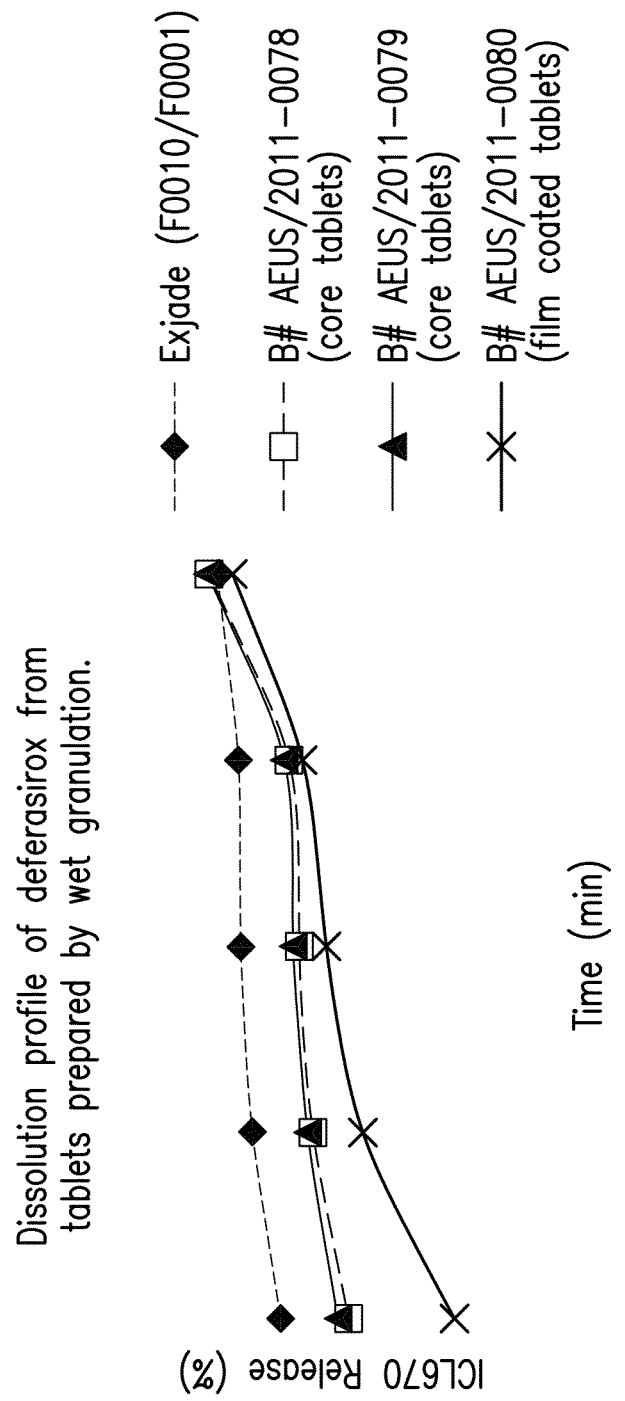

In accordance with the invented process, the wet granulation step is performed using 40-80% by weight of deferasirox, a poorly soluble drug with PVP K-30™ as a binding agent, Avicel™ PH 101 as a filler, crospovidone as a disintegrating agent and SLS or Poloxamer as a solubilizing agent. Water was used as granulation media. The granules were mixed with external excipients, e.g., Avicel™ PH102, crospovidone, Aerosil™ as glidant and magnesium stearate as an anti-sticking agent. The final granules were compressed into tablets and enterically coated using Acryl-EZE™ 93F, a Eudragit™ based polymer. The tablets has shown optimal hardness, friability and disintegration time. The dissolution profile of the coated deferasirox tablet is bioequivalent to the commercial Exjade (deferasirox) tablets, as shown in FIG. 2.

Figure 3:
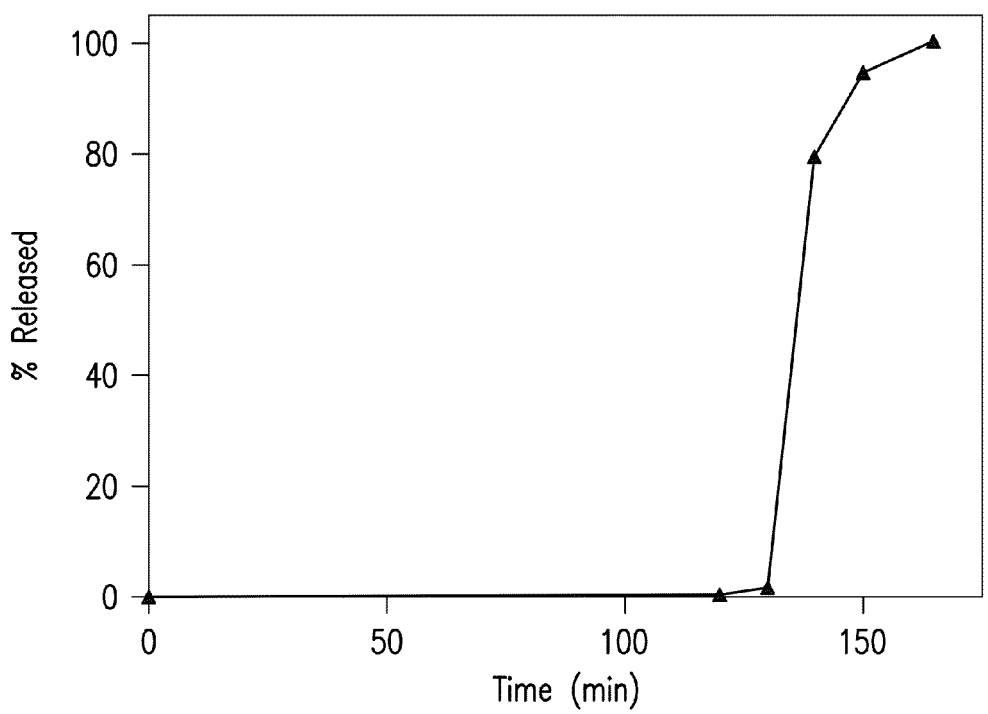
Figure 4:
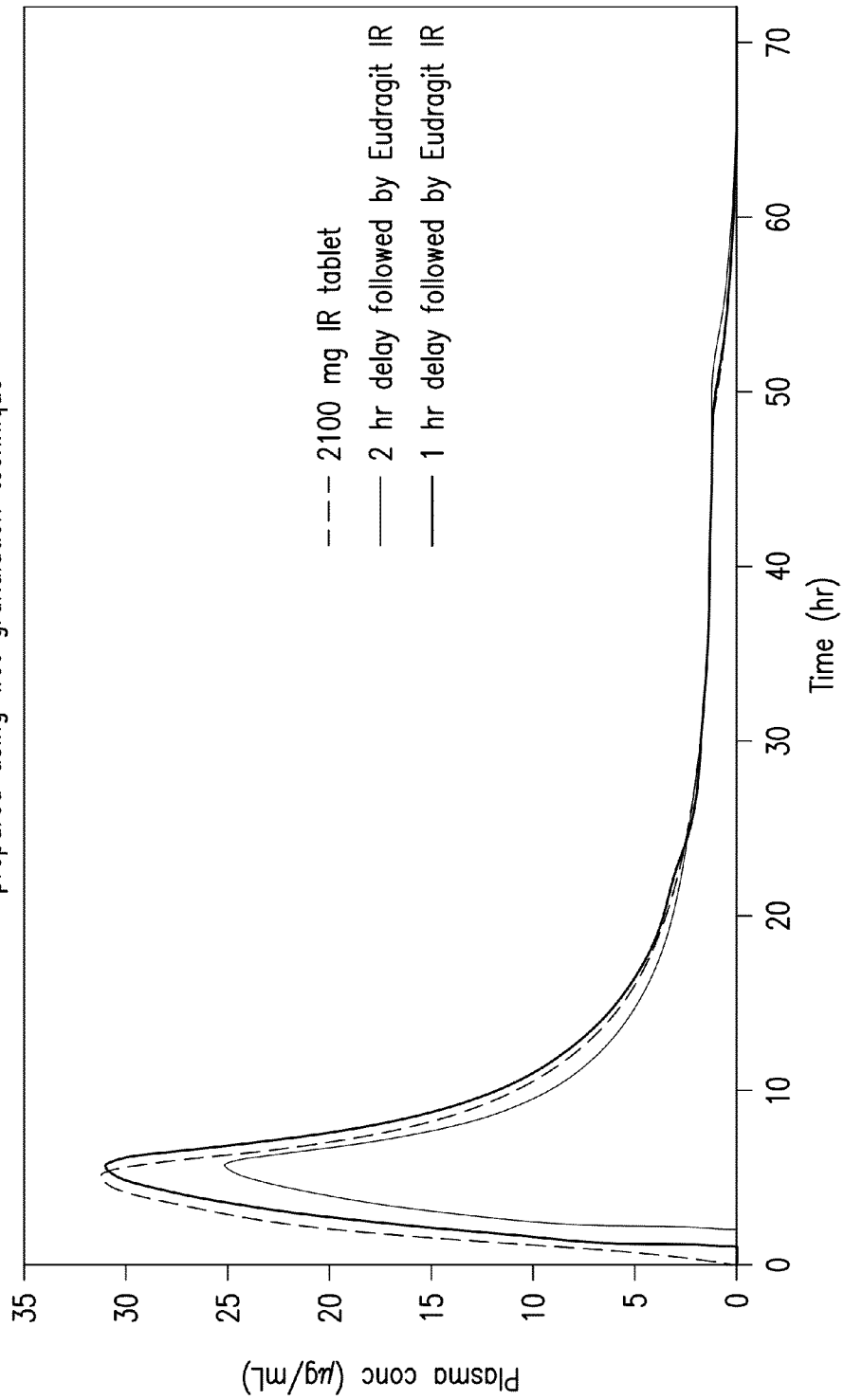
FIG. 4 summarizes the actual pharmacokinetic profiles of the commercial deferasirox tablets as well as those prepared using wet granulation technique FIG. 5 summarizes the dissolution profile of deferasirox capsule consisting of pellets prepared by extrusion spheronization.
Figure 5:
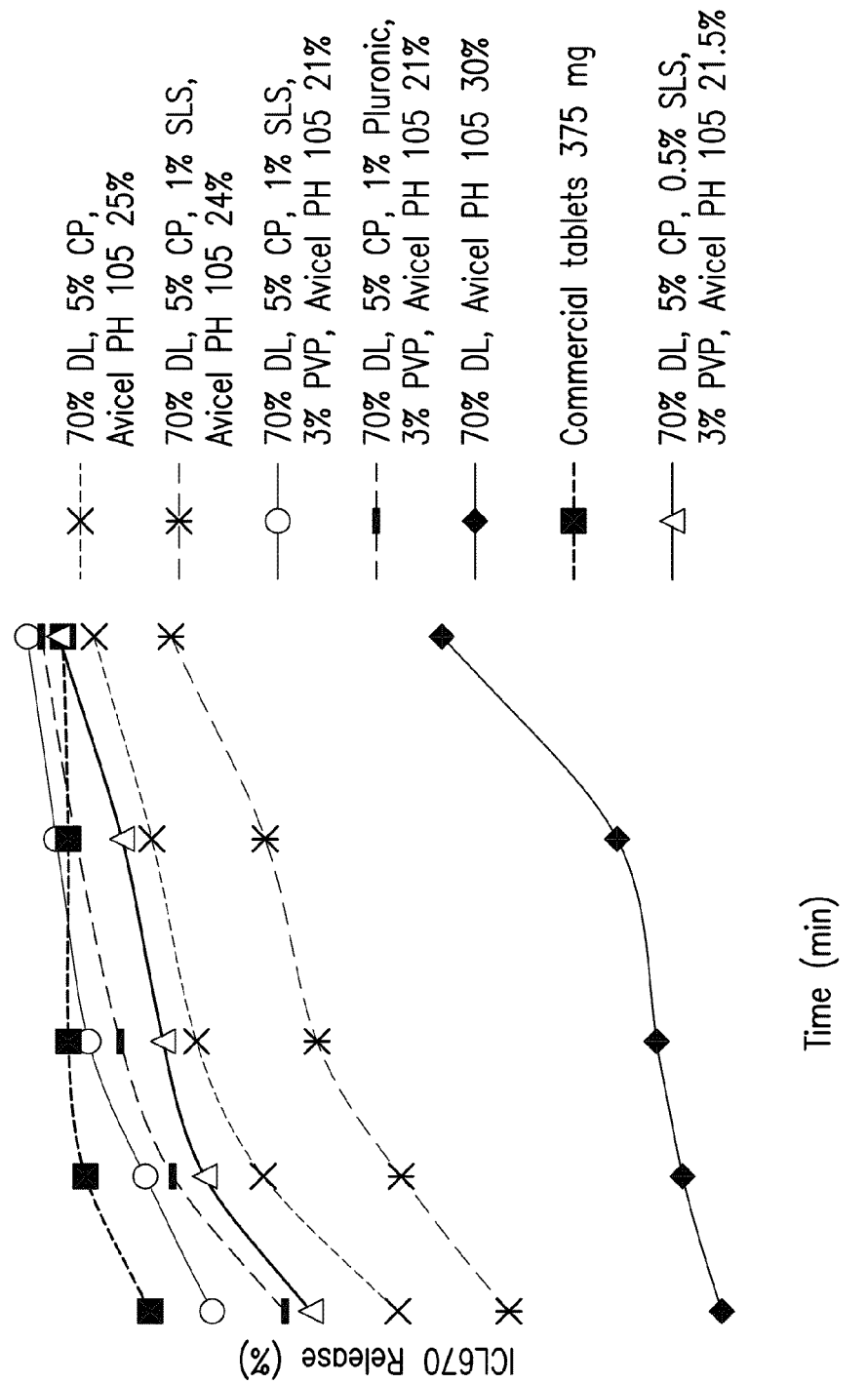
Figure 6:
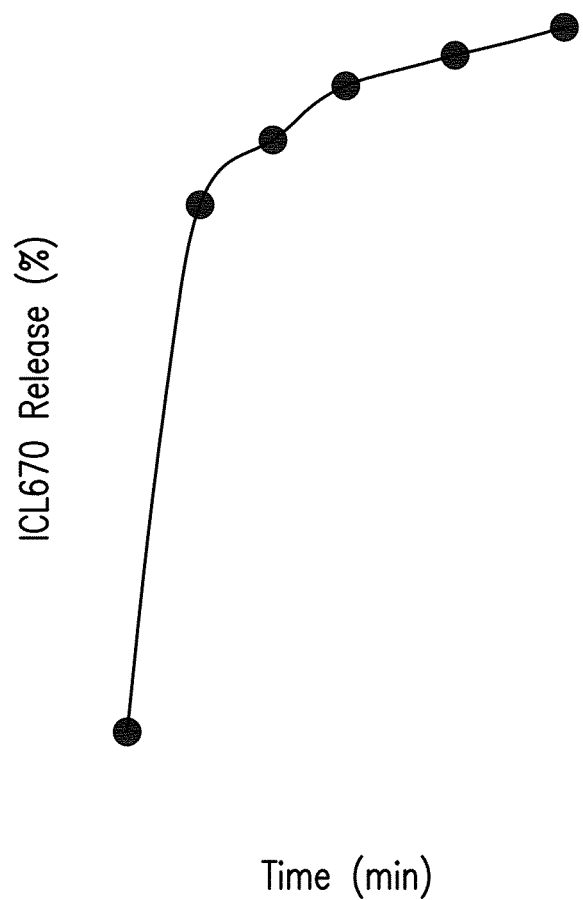
FIG. 6 summarizes the dissolution profile of deferasirox capsules consisting of enteric coated pellets prepared by extrusion spheronization.

Furthermore, in a related embodiment, the present invention provides a formulation with a full enteric coating. The enteric coating compris Opydrye® 03K19229 and Acryl-EZE™ was applied to a deferasirox tablet core at level of 5-15% by weight gain. An addition of sub-coating, such as Opydry™ 03K19229, enhanced the effectiveness of enteric coating. Full enteric protection is achieved after greater than 5% by weight gain. No major impact on deferasirox drug release was observed for enteric-coated deferasirox tablets after two hours acid treatment. Except for 10 minutes of the delay initially, the deferasirox drug release profiles are comparable to commercial Exjade™ (deferasirox) product, as shown in FIG. 3.

In general, after reaching the small intestine, the enteric coated tablets release the drug slowly. However, in the present invention, the use of unique polymer, for example PVP, as binder produces fast release of drug without any significant lag time. This will be helpful for achieving bioequivalency of the formulation as compared to reference product, which is a non-enteric dispersible tablet.

The medicament of the invention may be in any suitable form including. e.g. tablets, pellets, granules, multi-particulates, beads, mini-tabs, spherules, beadlets, microcapsules, milli-spheres, nano-capsules, micro-spheres, platelets or capsules depending upon the desired route of delivery.

An embodiment provides that the medicaments such as pellet and micro-particulates are filled in capsules, caplets or the like for oral delivery.

In another embodiment, the deferasirox medicament is packaged for use by the patient or caregiver. For example, the medicament can be packaged in a foil or other suitable package and is suitable for mixing into a food product (e.g. applesauce and other food vehicles) or into a drink for consumption by a patient.

B. Manufacturing Multi-Particulates Using a Extrusion Spheronization

In a separate exemplary embodiment, the present invention provides a process for the preparation of a coated deferasirox tablet, which comprises the steps:

(i) mixing deferasirox or a pharmaceutically acceptable salt and at least one pharmaceutically acceptable excipient;
(ii) wet-granulating the mixture obtained in step (i) in a high shear granulator;
(iii) extruding and spheronizing the wet granulates obtained in step (ii);
(iv) drying the extruded and spheronized pellets; and
(v) coating the pellets.

Accordingly, manufacturing deferasirox multi-particulates using a fluidized process technique or other pelletization techniques includes but is not limited to the following considerations:

a) Pre-wetting: Water is evenly distributed to the dry blend of drug and Avicel™ PH105 in a high shear granulator.

b) Pelletization: The pre-wetted blend was pelletized by mechanical and gravitational forces acting on the blend while being processed. Moisture (water) was constantly applied. Once the pellets reached the desired particle size range, a small percentage of the dry blend (or excipient alone) was incorporated on the pellets to stop growth and smooth the pellet surface.

c) Drying: The drying of the pellets was performed in a fluid-bed processor The pellets were dried to moisture content below 3% by weight.

The following examples illustrate aspects of the invention and are not a limitation on the present invention. Formulations for preparing tablets are set out below. In one aspect the tablets are formulated utilizing enteric coatings.

Example 1

Enteric Coated Wet Granulated Deferasirox Tablets Comprising a Surfactant, Sodium Lauryl Sulfate (SLS)

| Granulation | |
| --- | --- |
| Internal phase | |
| Ingredient | Weight % (range) |
| Deferasirox | 55.97% |
| Avicel ™ PH 101/105 | 14.4% (5-25) |
| PVP K-30 ™ | 2.25% (1-5) |
| Crospovidone | 2% (1-5) |
| SLS | 0.375% (0-1) |
| External phase | |
| Ingredient | Weight % (range) |
| Dried Granules | 75% |
| Avicel ™ PH 102 | 18.5% (5-25) |
| Crospovidone | 5% (2-10) |
| Aerosil ™ | 0.5 ranges % (0.1-1) |
| Magnesium Stearate | 1% (0.1-2) |
| Subcoating | |
| Opadry ™ 03K19229 | 1% (0-2) |
| Enteric coating | |
| Eudragit ™ (Acryl EZE 93F) | 7% (5-20) |

Example 2

Enteric Coated Wet Granulated Deferasirox Tablets Comprising a Poloxamer (Pluronic™ F68 Grade)

| Granulation | |
|---|---|
| Internal phase | |
| Ingredient | Weight % (range) |
| Deferasirox | 55.97% |
| Avicel ™ PH 101/105 | 14.4% (5-25) |
| HPMc ™ 3 cps | 2.25% (1-5) |
| Crospovidone | 2% (1-5) |
| Pluronic ™ | 0.375 % (0-1) |
| External phase | |
| Ingredient | Weight % (range) |
| Dried Granules | 75% |
| Avicel ™ PH 102 | 18.5% (5-25) |
| Crospovidone | 5% (2-10) |
| Aerosil ™ | 0.5 ranges % (0.1-1) |
| Magnesium Stearate | 1% (0.1-2) |
| Subcoating | |
| Opadry ™ 03K19229 | 1% (0-2) |
| Enteric coating | |
| Eudragit ™ (Acryl EZE ™ 93F) | 7% (5-20) |

Example 3

Composition of Deferasirox Pellets Manufactured by Extrusion-Spheronization Granulation

| Ingredient | Weight % (range) |
|---|---|
| Deferasirox | 60-80% |
| Avicel ™ PH 101/105 | 8-32% |
| PVP K-30 ™ or | 2-5% |
| HPMC ™ 3 cps or | |
| HPC EXF ™ | |
| Crosspovidone | 5% |
| SLS/Poloxamer ™ | 1-2% |
| Enteric coating | |
| Eudragit ™ (Acryl EZE ™ 93F) | 5-20% |

Example 4

Composition of Deferasirox Pellets Manufactured by Fluidized Technique

| Granulation | |
|---|---|
| Ingredient | Weight % |
| ICL670 ™ | 70-80% |
| Avicel ™ PH 105 | 20-30% |

The compositions of the present invention and manufacturing processes provide coated tablets of Exjade (deferasirox) and thereby minimize local GI irritation. When compared to the dispersible Exjade (deferasirox) tablets having a 29.4% drug load. The present invented methods and corresponding invented improved deferasirox formulations increase the drug load for producing swallowable (ingestable) deferasirox tablets that improve patient compliance.

Example 5

Deferasirox Coated Tablets Prepared by Wet Granulation Using Non-Functional Coating

| | Deferasirox Tablets: Invented doses Variant A | | | |
|---|---|---|---|---|
| Component | % (w/w) (range) | mg/648 mg tab | mg/324 mg tab | mg/162 mg tab |
| Deferasirox | 55.56 | 360.00 | 180.00 | 90.00 |
| Microcrystalline cellulose PH101 ™ | 15.09 | 97.81 | 48.91 | 24.45 |
| Microcrystalline cellulose PH102 ™ | 18.00 | 116.64 | 58.32 | 29.16 |
| Poly Vinyl Pyrrolidone K-30 ™ | 2.25 | 14.58 | 7.29 | 3.65 |
| Crospovidone | 7.00 | 45.36 | 22.68 | 11.34 |
| Pluronic ™ F68 | 0.10 | 0.65 | 0.32 | 0.16 |
| Aerosil ™ | 0.50 | 3.24 | 1.62 | 0.81 |
| Magnesium Stearate | 1.50 | 9.72 | 4.86 | 2.43 |
| Total | 100.00 | 648.00 | 324.00 | 162.00 |
| Coating | | | | |
| Opadry ™ Blue | 3.00 | 19.44 | 9.72 | 4.86 |
| Final tablet weight | 103.00 | 667.44 | 333.72 | 166.86 |

| | Invented Deferasirox Pediatric Granule Doses Variant A | | | |
|---|---|---|---|---|
| Component | % (w/w) | mg/720 mg tab | mg/360 mg tab | mg/180 mg tab |
| Deferasirox | 55.56 | 400.00 | 200.00 | 100.00 |
| Microcrystalline cellulose PH101 ™ | 15.09 | 108.68 | 54.34 | 27.17 |
| Microcrystalline cellulose PH102 ™ | 18.00 | 129.60 | 64.80 | 32.40 |
| Polyvinyl Pyrrolidone K-30 ™ | 2.25 | 16.20 | 8.10 | 4.05 |
| Crospovidone | 7.00 | 50.40 | 25.20 | 12.60 |
| Pluronic ™ F68 | 0.10 | 0.72 | 0.36 | 0.18 |
| Aerosil ™ | 0.50 | 3.60 | 1.80 | 0.90 |
| Magnesium Stearate | 1.50 | 10.80 | 5.40 | 2.70 |
| Total | 100.00 | 720.00 | 360.00 | 180.00 |

Summary of Deferasirox Variants Used in Clinical Pharmokinetic (PK) Study

| Materials | Variant A Qty (%) | Variant B Qty (%) | Variant C Qty (%) |
|---|---|---|---|
| Deferasirox | 55.56 | 55.56 | 54.08 |
| Cellulose microcrystalline | 15.09 | 14.19 | 13.82 |
| Crospovidone | 7.00 | 7.0 | 6.81 |
| Polyvinylpyrrolidone K30 ™ | 2.25 | 2.25 | 2.19 |
| Poloxamer ™ 188 | 0.10 | 1.00 | 0.97 |
| Cellulose MKR ™ GRN | 18.00 | 18.00 | 17.52 |

-continued

| Materials | Variant A Qty (%) | Variant B Qty (%) | Variant C Qty (%) |
|---|---|---|---|
| Aerosil ™ | 0.50 | 0.50 | 0.49 |
| Magnesium stearate | 1.50 | 1.50 | 1.46 |
| Eudragit ™ L 100-55 | — | — | 2.17 |
| Hypromellose 5 cps | — | — | 0.11 |
| Sodium hydroxide | — | — | 0.03 |
| Triethyl citrate | — | — | 0.28 |
| Polysorbate ™ 80 | — | — | 0.002 |
| Glycerol monostearate | — | — | 0.06 |
| Total weight (mg) | 100.00 | 100.00 | 100.00 |

Tablet properties

| | Variant A | Variant B | Variant C |
|---|---|---|---|
| Tooling | 19 × 7.5 Ovaloid | 19 × 7.5 Ovaloid | 19 × 7.5 Ovaloid |
| Mean weight (mg) | 910.24 | 916.22 | 903.62 |
| Compression force (kN) | 25.00 | 25.00 | 25.00 |
| Mean hardness (N) | 267.60 | 231.70 | 236.70 |
| % friability | 0.00 | 0.02 | 0.11 |
| Dissolution Time (DT, min.) with discs | 3.42 | 5.45 | 6.45 |

Granule Size for Deferasirox Variant A Formulation Corresponding to a Representative Batch for a Pilot Phase

| | | Water (%) | Water addition time (min) | LOD (%) | Bulk Density (g/ml) | Tap Density (g/ml) | 1.4 | 1.0 | 0.71 |
|---|---|---|---|---|---|---|---|---|---|
| Clinical Deferasirox Batch | 5 Kg | 26 | 7 | | 0.49 | 0.85 | 0 | 7.4 | 17.1 |
| | | | | | | | 0.00% | 7.39% | 17.08% |
| Pilot phase DoE batch | 20 Kg | 26 | 7 | | 0.47 | 0.66 | 0 | 0 | 3.7 |
| | | | | | | | 0.00% | 0.00% | 7.43% |

| | | 0.5 | 0.25 | 0.18 | 0.125 | 0.09 | Pan | Total (g or %) |
|---|---|---|---|---|---|---|---|---|
| Clinical Deferasirox Batch | 5 Kg | 10.9 | 14.3 | 7.1 | 10.6 | 9.4 | 23.3 | 100.0 |
| | | 10.89% | 14.29% | 7.09% | 10.59% | 9.39% | 23.28% | 100.00% |
| Pilot phase DoE batch | 20 Kg | 7.6 | 9.2 | 5.2 | 6.3 | 6.1 | 12.7 | 49.8 |
| | | 15.26% | 18.47% | 10.44% | 12.65% | 10.24% | 25.50% | 100.00% |

Patient Data from the clinical study are summarized in Table 2.

TABLE 2

PK results from deferasirox tablets prepared by wet granulation with non-functional coating

| | Cmax | | | AUC | | |
|---|---|---|---|---|---|---|
| | A | B | C | A | B | C |
| 0501_00001 | 0.906 | 1.239 | 0.112 | 0.891 | 1.339 | 0.276 |
| 0501_00008 | 1.576 | 1.897 | 1.554 | 1.624 | 1.449 | 1.475 |
| 0501_00013 | 1.347 | 1.516 | 1.046 | 1.433 | 1.785 | 1.305 |
| 0501_00020 | 0.952 | 1.153 | 1.202 | 0.943 | 1.087 | 1.154 |
| 0501_00023 | 1.727 | 1.225 | 1.765 | 1.567 | 0.974 | 1.574 |
| 0501_00026 | 0.981 | 1.133 | 1.420 | 0.963 | 0.998 | 1.018 |
| 0501_00027 | | 2.293 | 1.122 | | 2.477 | 1.015 |
| 0501_00031 | 1.820 | 2.482 | 1.664 | 2.031 | 3.152 | 2.060 |
| 0501_00035 | 1.778 | 1.517 | 1.672 | 1.246 | 1.015 | 1.249 |
| 0501_00038 | 1.412 | 1.858 | 1.350 | 1.673 | 2.233 | 1.126 |
| 0501_00049 | 1.714 | 2.233 | 1.467 | 1.929 | 1.525 | 1.752 |
| 0501_00052 | 1.176 | 1.244 | 1.538 | 1.774 | 1.564 | 1.538 |
| 0501_00053 | 1.057 | 1.340 | 1.091 | 0.894 | 1.269 | 1.138 |
| 0501_00054 | 0.781 | 0.769 | 0.369 | 0.791 | 0.789 | 0.380 |
| 0501_00055 | 1.652 | 1.326 | 1.380 | 2.039 | 1.094 | 2.672 |
| 0501_00075 | 1.317 | 1.268 | 1.380 | 1.010 | 1.388 | 1.318 |
| 0501_00088 | 1.604 | 1.580 | 0.921 | 1.552 | 1.452 | 1.075 |
| 0501_00093 | 1.689 | 1.713 | 1.976 | 1.767 | 1.924 | 1.472 |
| 0501_00104 | 1.827 | 1.556 | 1.519 | 1.489 | 1.360 | 1.495 |
| 0501_00107 | 1.352 | 1.060 | 0.725 | 1.370 | 1.357 | 0.614 |

The dissolution profile for clinical deferasirox variants A, B, and C (500 MG) is highlighted in Table 3.

TABLE 3

Dissolution data for Clinical Variants A, B, and C (500 mg).

| | | 90% CI | |
|---|---|---|---|
| Treatment | Geo-mean ratio | Lower | Upper |
| A: 500 mg tablet with 0.1% Pluronic ™ | 1.38 | 1.18 | 1.62 |
| B: 500 mg tablet with 1.0% Pluronic ™ | 1.43 | 1.22 | 1.67 |

TABLE 3-continued

Dissolution data for Clinical Variants A, B, and C (500 mg).

| Treatment | Geo-mean ratio | 90% CI Lower | 90% CI Upper |
|---|---|---|---|
| C: 500 mg tablet with 1.0% Pluronic ™ + modified-release enteric coating | 1.15 | 0.99 | 1.35 |

Data for $C_{max}$ were comparable to those for AUC.
Median $T_{max}$ (3-4 hrs) appeared to be similar with all formulations.
Deferasirox PK was slightly less variable with variants A, and B (CV 23-38%), and slightly more variable with variant C (CV 54-61%) as compared to a conventional marketed commercial formulation (CV 31-49%).
PK data with the current formulation in this study were consistent with data from previous studies.

Example 6

High Load Deferasirox Formulation No Food Effect Studies

Six clinical studies have been initiated with corresponding pharmacology studies in healthy adult volunteers. Four studies have been completed and two studies are ongoing. In the initial clinical pharmacology study for variant selection (study 1), the tablet variant selected for development displayed suprabioavailability: both AUC and $C_{max}$ for the invented deferasirox formulation were approximately 40% higher compared to the current dispersible tablet (DT) at a single dose of 1500 mg. Therefore, the subsequent clinical pharmacology studies used strength-adjusted formulations (400 mg granules and 360 mg FCT to match the 500 mg DT), in line with EMA/618604/2008 Rev. 7, which states that "If suprabioavailability is found, development of a lower dosage strength should be considered".
Study 2 (pivotal study with FCT) and study 3 (pilot study with granules) both demonstrated fully equivalent exposure with an $AUC_{last}$ ratio of 100%. However. $C_{max}$ did not meet the standard bioequivalence criteria (as summarized in Table 4): values were higher for both strength-adjusted formulations. The food effect study 4 (granules) showed overall equivalence of the administration with a soft food (apple sauce or yogurt) or with a low-fat meal when compared to fasting intake with water. The exposure after administration with a high-fat meal was close to the equivalence limits of 80% to 125% for $AUC_{last}$.

TABLE 4

Summary of pharmacokinetic comparisons for invented deferasirox formulation

| Study No. | N | deferasirox dose [mg] (form) | food | AUClast ratio (90% CI) | Cmax ratio (90% CI) |
|---|---|---|---|---|---|
| Completed Studies ||||||
| 1 | 2 | 1500 (F)/ | fasted/fasted | 1.38 | 1.39 |
|   | 0 | 1500 (DT) |  | (1.179-1.620) | (1.164-1.661) |
| 2 | 3 | 1080 (F)/ | fasted/fasted | 1.00 | 1.30 |
|   | 2 | 1500 (DT) |  | (0.932-1.078) | (1.203-1.400) |
| 3 | 2 | 1200 (G)/ | fasted/fasted | 1.00 | 1.18 |
|   | 0 | 1500 (DT) |  | (0.915-1.099) | (1.050-1.323) |
| 4 | 2 | 1200 (G)/ | applesauce/ | 0.996 | 0.972 |
|   | 4 | 1200 (G) | water | (0.934-1.063) | (0.891-1.061) |
|   |   | 1200 (G)/ | yogurt/water | 0.986 | 0.988 |
|   |   | 1200 (G) |  | (0.924-1.052) | (0.905-1.077) |
|   | 2 | 1200 (G)/ | breakfast/ | 0.917 | 0.887 |
|   | 4 | 1200 (G) | water | (0.845-0.995) | (0.789-0.997) |
|   |   | 1200 (G)/ | high-fat | 1.194 | 0.949 |
|   |   | 1200 (G) | breakfast/ water | (1.099-1.298) | (0.843-1.069) |
| Ongoing Studies (results expected by Dec 2013) ||||||
| 5 |   | 1080 (F)/ | fed/fasted | TBD | TBD |
|   |   | 1080 (F) |  |  |  |
| 6 |   | 1200 (G)/ | fasted/fasted | TBD | TBD |
|   |   | 1500 (DT) |  |  |  |

DT: dispersible tablets (current formulation);
F: film-coated tablets;
G: granules;
N = number of subjects.
Study 3 also tested dose linearity (at 400 mg/800 mg/1200 mg) for the granules.
Values outside the equivalence limits [0.8-1.25] are highlighted in bold The two remaining clinical pharmacology studies (to be conducted in 2H2013) aim to confirm the comparative bioavailability results for the granules, and to test the food effect for the FCT.

The new Exjade formulations represent a significant improvement in patient care and support compliance with chelation therapy because of the improved pharmaceutical properties and because of the changes in composition. These improvements are expected to provide for a positive benefit risk due to the importance of compliance/adherence to chelation therapy for patients with chronic iron overload aged 2 years and older:

- a lower inter-subject variability in exposure (CV % geometric mean in study F2102 for FCT and DT: $AUC_{last}$ 39.2% vs 49.7%, Cmax 27.5% vs 33.4%, respectively) and the absence of a substantial food effect (study 4) suggest that the new formulations achieve a more predictable dose-exposure relationship in clinical practice.
- the absence of a substantial food effect (study 4) which obviates the requirement to take the drug on an empty stomach at least 30 minutes before food and therefore allows patients more convenience and flexibility in the scheduling and administration of their daily dose.
- a more palatable alternative to the currently approved dispersion, particularly for elderly and pediatric patients (an aspect that was investigated in one of the measures of the currently approved Exjade EU PIP).
- The currently approved Exjade tablet is formulated with sodium lauryl sulphate, which may be associated with gastrointestinal tract irritation. Exjade currently also contains lactose and so is not recommended in patients with rare hereditary problems of galactose intolerance, the Lapp lactase deficiency, glucose-galactose malabsorption or severe lactase deficiency. Novartis believes the exclusion of lactose and sodium lauryl sulfate in the new formulations will improve the gastrointestinal tolerability of the product. This is supported by the recently completed one year study 2209 where NTDT patients in the placebo arm, which contained the same excipients as the currently marketed Exjade formulation, reported GI adverse event rates that were comparable to the active treatment arm (42.9% for placebo vs. 36.4% for Exjade 10 mg/kg).

While the 90% CI for Cmax with both the FCT (in the pivotal study 2) and the granules (in the pilot study) were not fully contained within the equivalence limits of 80% to 125%, the observed differences in $C_{max}$ not clinically meaningful for the new formulations of this innovator drug based on the following rationale:

total drug exposure (AUC) is the key parameter predicting safety and efficacy of deferasirox; chelation efficacy for iron chelators is commonly accepted to be related to AUC. In a 24-hour PK study following a single 35 mg/kg dose of oral deferasirox that was published by Chirnomas et al (2009), patients with inadequate response to deferasirox had significantly lower systemic drug exposure compared with control patients (P<0.00001). $C_{max}$, volume of distribution/bioavailability (Vd/F), and elimination half-life (t(½)) were not different between the groups.

no effect on the QT interval (a typical $C_{max}$-related toxicity) was observed in the thorough QT study (submitted with the original application in 2005): in that study, healthy volunteers (in whom exposure is higher than in iron-overloaded patients) were given doses of up to 40 mg/kg in order to achieve high Cmax levels the range of Cmax values observed in previous healthy volunteer studies with over 200 subjects is consistent with the range of $C_{max}$ values observed with the new formulations (see below)

a large amount of safety, efficacy and exposure data exist for the current formulation (see below for details)

in previously submitted patient studies, only minor safety findings such as nausea and headaches were noted at $T_{max}$ (see below for details)

a statistical analysis to correlate pharmacokinetic parameters (Ctrough as a proxy of AUC, C2h as a proxy for Cmax) with renal effects in the large, one year patient study A2409 indicates that creatinine changes are more strongly correlated with AUC than with Cmax (see below for details)

Exjade™ (deferasirox) is titrated based on efficacy and tolerability: the recommended starting dose is 20 mg/kg/day, with up-titration recommended in 5-10 mg/kg steps every 3-6 months. Therefore, patients would only be exposed to the highest approved dose (40 mg/kg/day for the current formulation) after an extended period of up-titration with confirmed tolerability the absence of a significant food effect results in a lower risk of increased exposure when the drug is taken with a meal. With the currently approved DT formulation, ingestion of 20 mg/kg with a high fat meal (previous study for commercially marketed formulation) resulted in an average Cmax of 138 µM in healthy volunteers, whereas dispersion in water (study 2120) resulted in a lower Cmax of 71 µM in healthy volunteers. In the patient study A0105F, exposure nearly doubled (to a variable extent) when Exjade was given after a high-fat breakfast. No such effect was observed with the new granule formulation (Table 4).

Figure 7A:
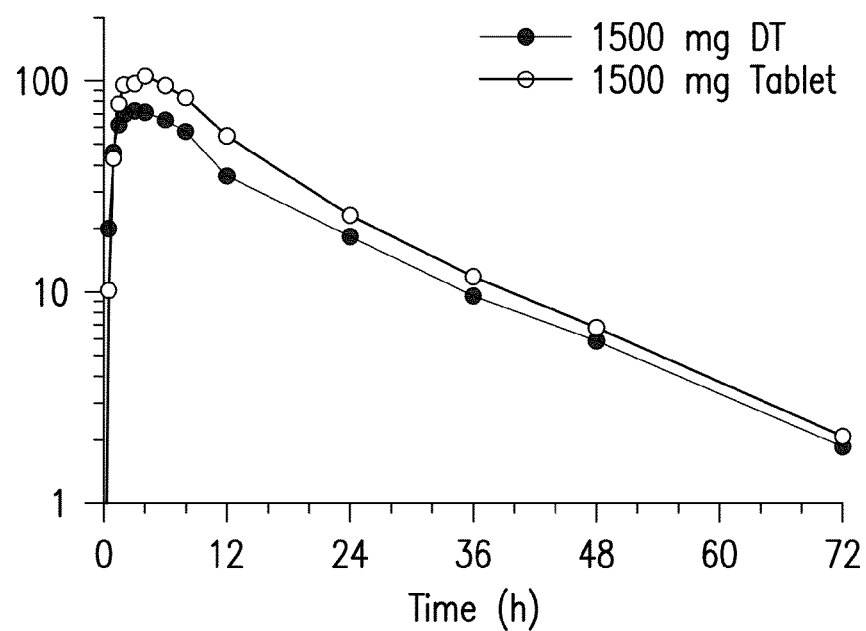
FIG. 7A, FIG. 7B, and FIG. 7C summarizes deferasirox mean concentration versus time profiles for the invented formulations.
Figure 7B:
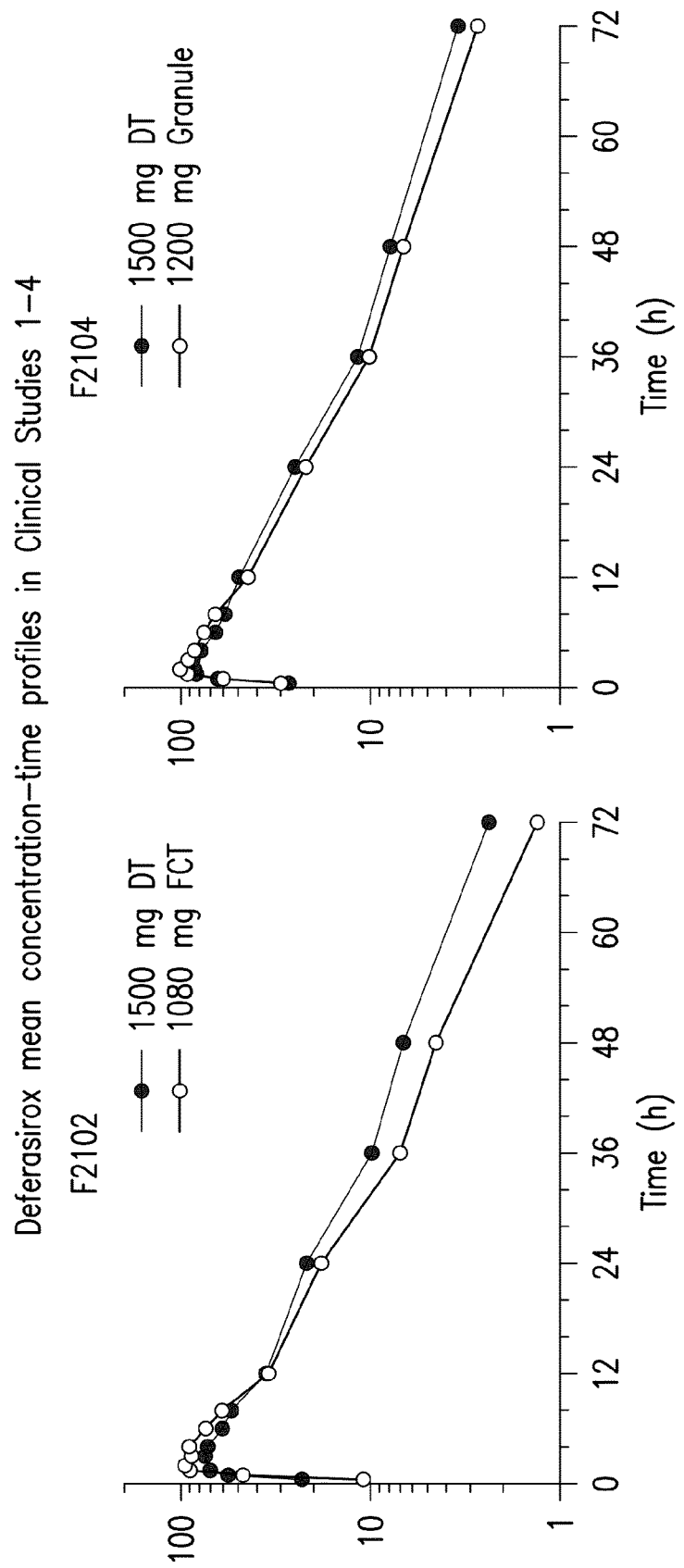
Figure 7C:
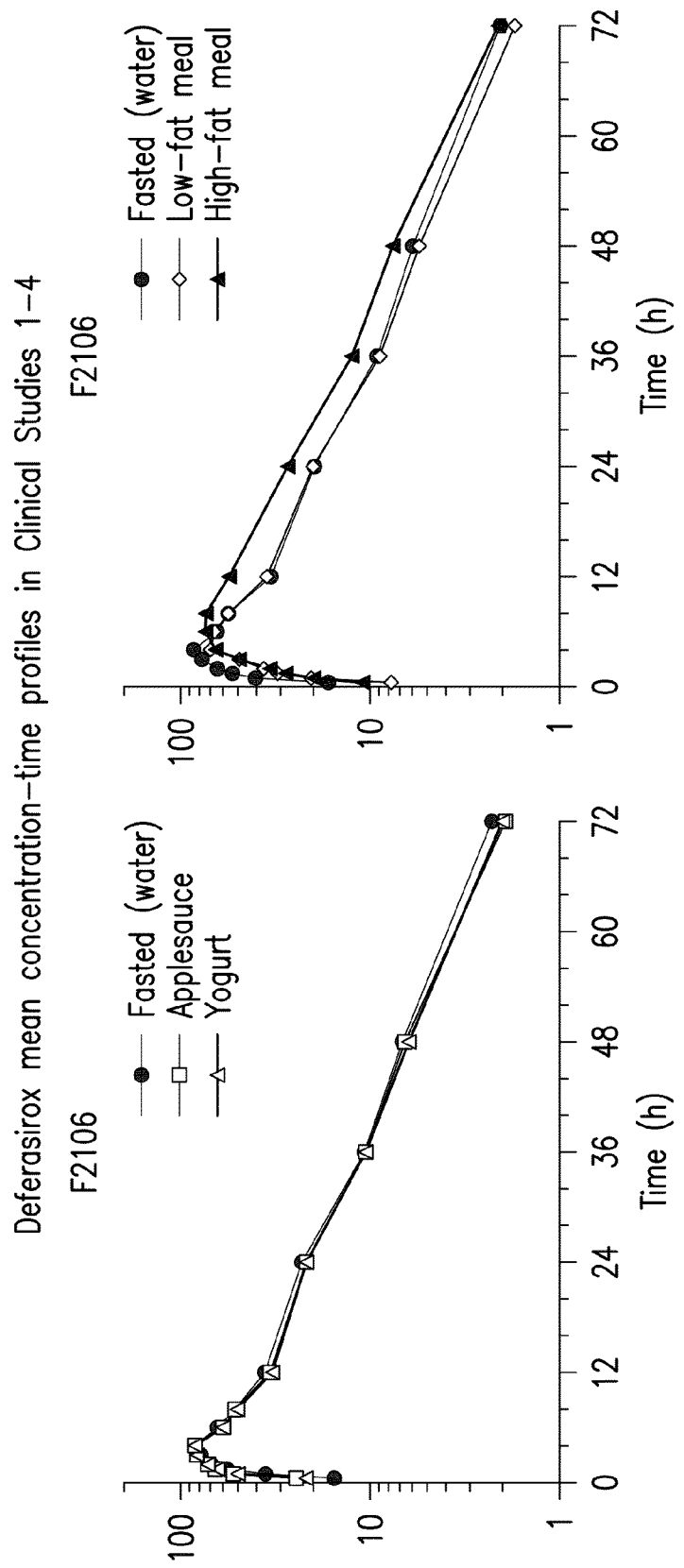

FIG. 7 summarizes mean concentration (µmol/L)-time profiles of the key pharmacokinetic results for studies 1 (non-strength-adjusted tablet comparison), 2 (pivotal strength-adjusted FCT study), 3 (pilot strength-adjusted granule study), and 4 (granule food-effect study).

Figure 8:
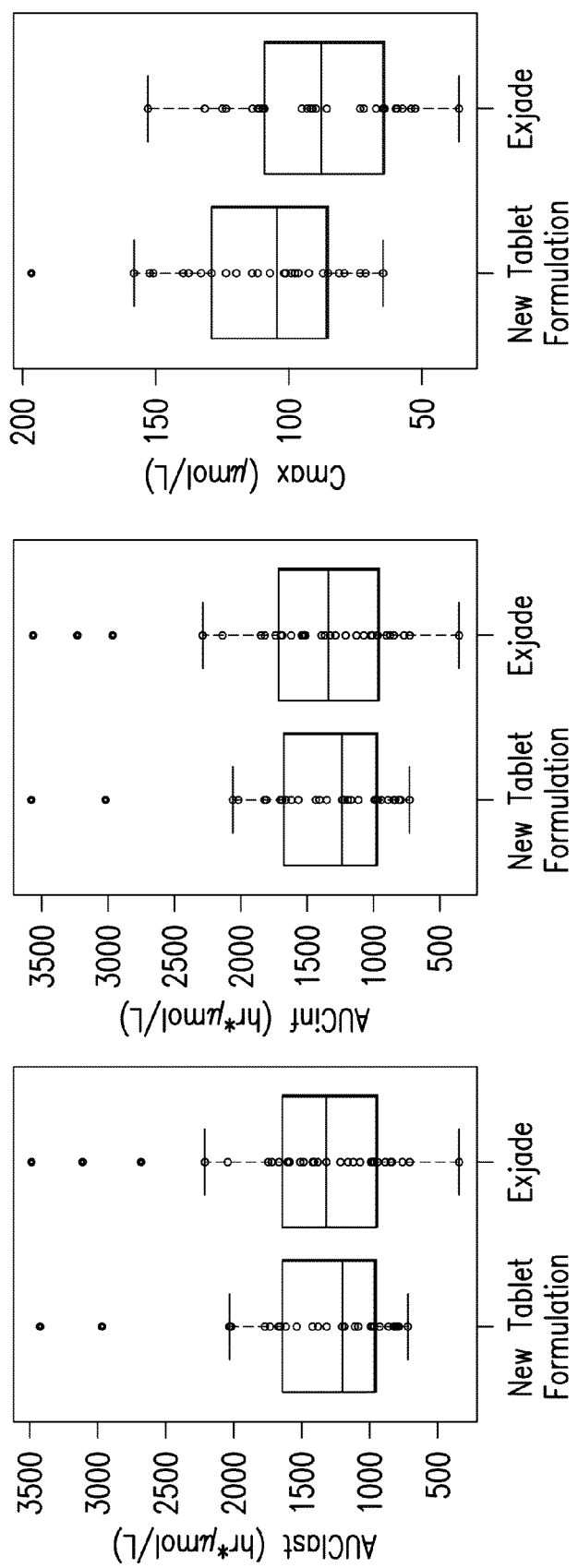
FIG. 8 summarizes inter-subject varabilities in pharmokinetic parameters $AUC_{last}$, $AUC_{inf}$, and $C_{max}$ for the invented formulations.

Individual $C_{max}$ values from Study 2 and Study 3 are within the range of historical $C_{max}$ values observed with the current commercially marketed DT formulation: FIG. 8 includes $C_{max}$ data from (1) previous CP studies in healthy subjects given 20 mg/kg deferasirox DT, (2) FCT treatment in Study 2, and (3) granule treatment in Study 3.

Figure 9:
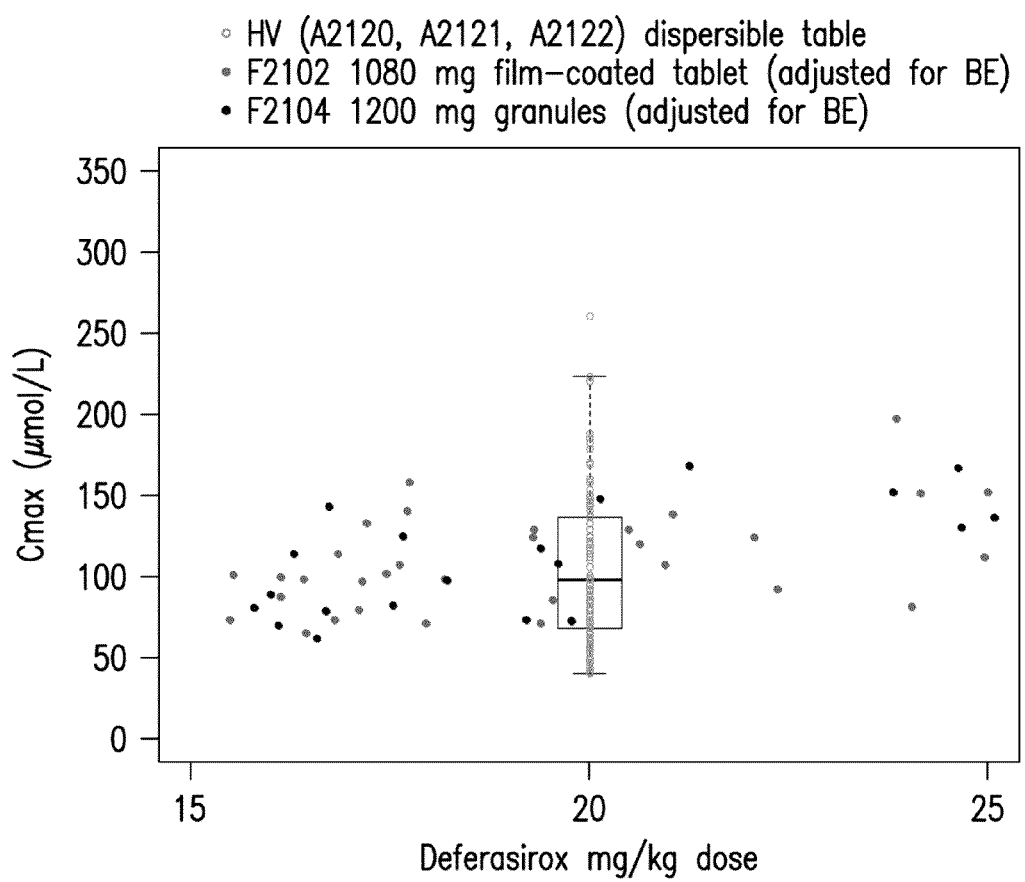
FIG. 9 summarizes a deferasirox $C_{max}$ comparison in the invented formulation versus commercially available formulation for healthy volunteers.
Figure 10:
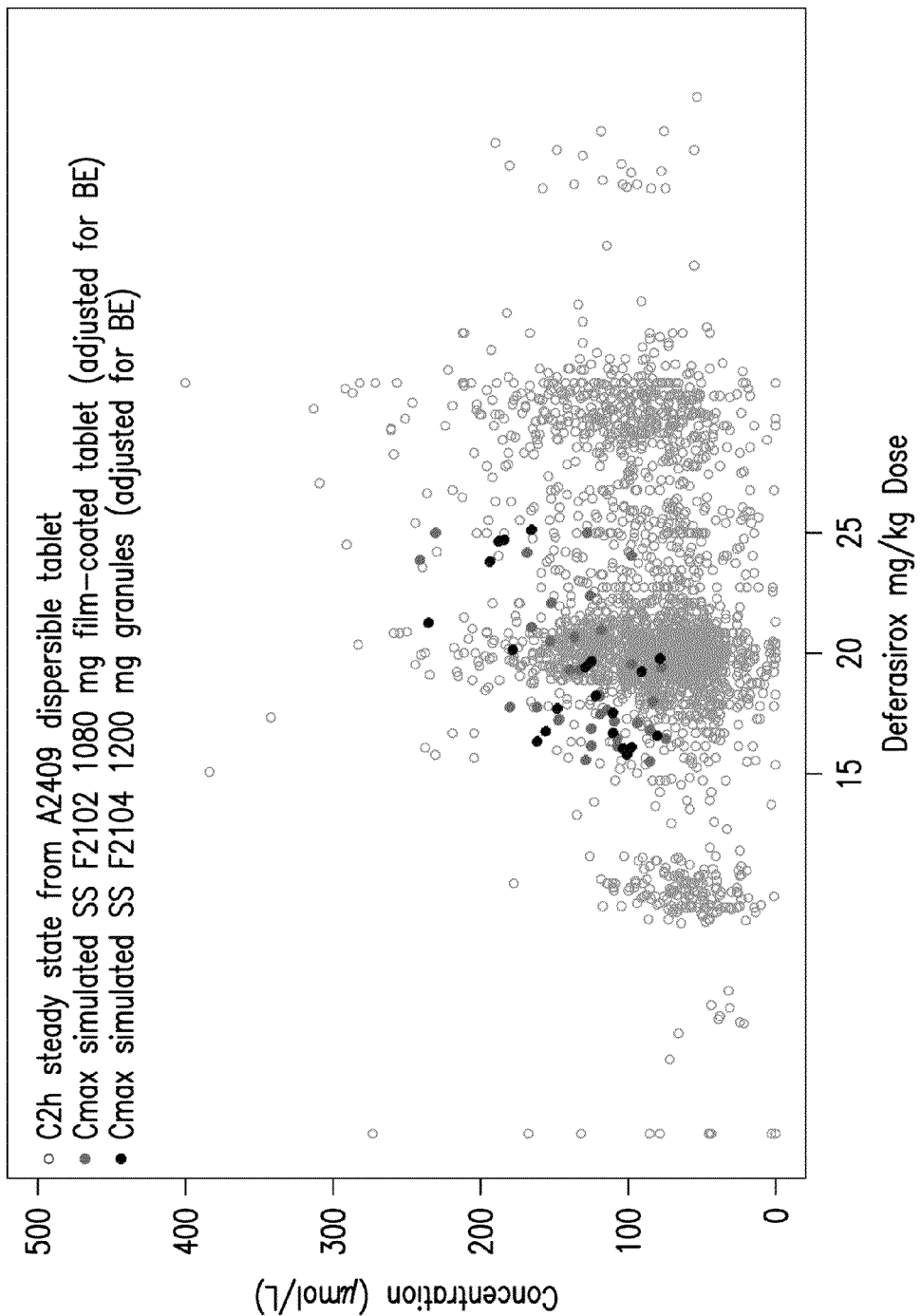
FIG. 10 summarizes steady state deferasirox C2h values versus Cmax for the invented formulation versus commercially available formulation.

Clinical data has been generated and analyzed from a one-year, open-label, single arm, multi-center trial evaluating the efficacy and safety of oral deferasirox formulation (20 mg/kg/day) in 1744 patients with transfusion dependent iron overload; thalassemia, MDS, SCD, and rare anemias (Study 7). Study 7 used sparse PK sampling: in addition to efficacy and safety data, deferasirox PK data were collected in a large sub-group of patients (~600) at pre-dose ($C_{trough}$, a proxy for AUC) and 2 hours post-dose (C2h; a proxy for Cmax) on day 1, week 12 and week 28. As shown in FIG. 9, the $C_{max}$ values for the new high load deferasirox formulations at steady-state (predicted by a nonparametric superposition approach) in studies 2 and 3 lie within the range of observed steady-state deferasirox C2h values with the current DT formulation. Of note, deferasirox exposure in healthy subjects is generally higher than in iron-overloaded patients; in addition, the sampling time point in Study 7 (C2h) underestimates $C_{max}$ (since deferasirox $T_{max}$ usually occurs between 2 and 4 hours post-dose). Since clinical safety data were assessed within this range of $C_{max}$, it is unlikely that $C_{max}$ observed with the new formulations would lead to additional safety issues.

Deferasirox Cmax values in healthy volunteers are generally higher than in patients. Two healthy volunteer studies in the initial registration package in 2005 were therefore reviewed for potential Cmax-related adverse events. In the thorough QT healthy volunteer study (which found no effect of Exjade on the QT interval), 44 volunteers received Exjade™ (deferasirox 40 mg/kg immediately after consumption of a high-fat breakfast to maximize $C_{max}$. $C_{max}$ averaged 256 µM (range 134-472 µM). Safety findings in these subjects were limited to GI symptoms (diarrhea/loose stools, flatulence, and nausea) in 18% of patients, and headache and dizziness in one patient each (2%). In a study (a randomized crossover study in 28 healthy volunteers to evaluate the bioequivalence of a single 20 mg/kg dose of Exjade™ dispersed in fruit juice or water), three HV subjects reported loose stools 2.5 to 5 hours after Exjade intake, each on two separate occasions, lasting for 5-30 minutes.

In addition, a new analysis of creatinine and creatinine clearance changes was performed to explore whether deferasirox-associated renal changes are a function of peak exposure ($C_{max}$) or of overall exposure (AUC). The analysis used data from the large multicenter study 7, in which $C_{trough}$ (a proxy of AUC) and deferasirox C2h (a proxy of $C_{max}$) was collected at multiple time points. Even though both PK parameters correlate with dose, the analyses summarized below indicate that renal functional changes are more closely associated with AUC than with $C_{max}$.

Based on study 7 data, the relationship between PK parameters at steady state ($C_{trough}$ and C2h) and serum creatinine was investigated by using a linear mixed model of log-transformed creatinine values (1990 observations at week 12 and 28) with patient included in model as a random effect. After log-transformation, baseline creatinine levels, C2h and $C_{trough}$ were included as predictors in the model. As shown in Table 5, a far higher slope (estimate) was observed for log ($C_{trough}$) than for log(C2h), indicating a higher correlation with Ctrough (a proxy of AUC) than with C2h (a proxy of $C_{max}$). For a 30% increase in $C_{max}$ (as observed for the FCT), the serum creatinine ratio would be 1.0087 (=1.3^0.03287) with upper bound of the 95% CI of 1.0127 (with all other factors held constant). The potential of multicolinearity for log(C2h) and log($C_{trough}$) was assessed in the statistical model described above and did not show any multicolinearity issue (Variance Inflation Factor (VIF)=1.56 and condition index<30).

TABLE 5

Linear mixed effect model of percent change in serum creatinine for deferasirox formulations

| Parameter | Estimate | Standard error | T value | Pr > \|t\| | Lower | Upper |
|---|---|---|---|---|---|---|
| Log (baseline creatinine) | 0.9593 | 0.01226 | 78.22 | <0.0001 | 0.9391 | 0.9795 |
| Log (C2h) | 0.03287 | 0.007786 | 4.22 | <0.0001 | 0.02005 | 0.04569 |
| Log ($C_{trough}$) | 0.06504 | 0.004803 | 13.54 | <0.0001 | 0.05713 | 0.07295 |

Figure 11:
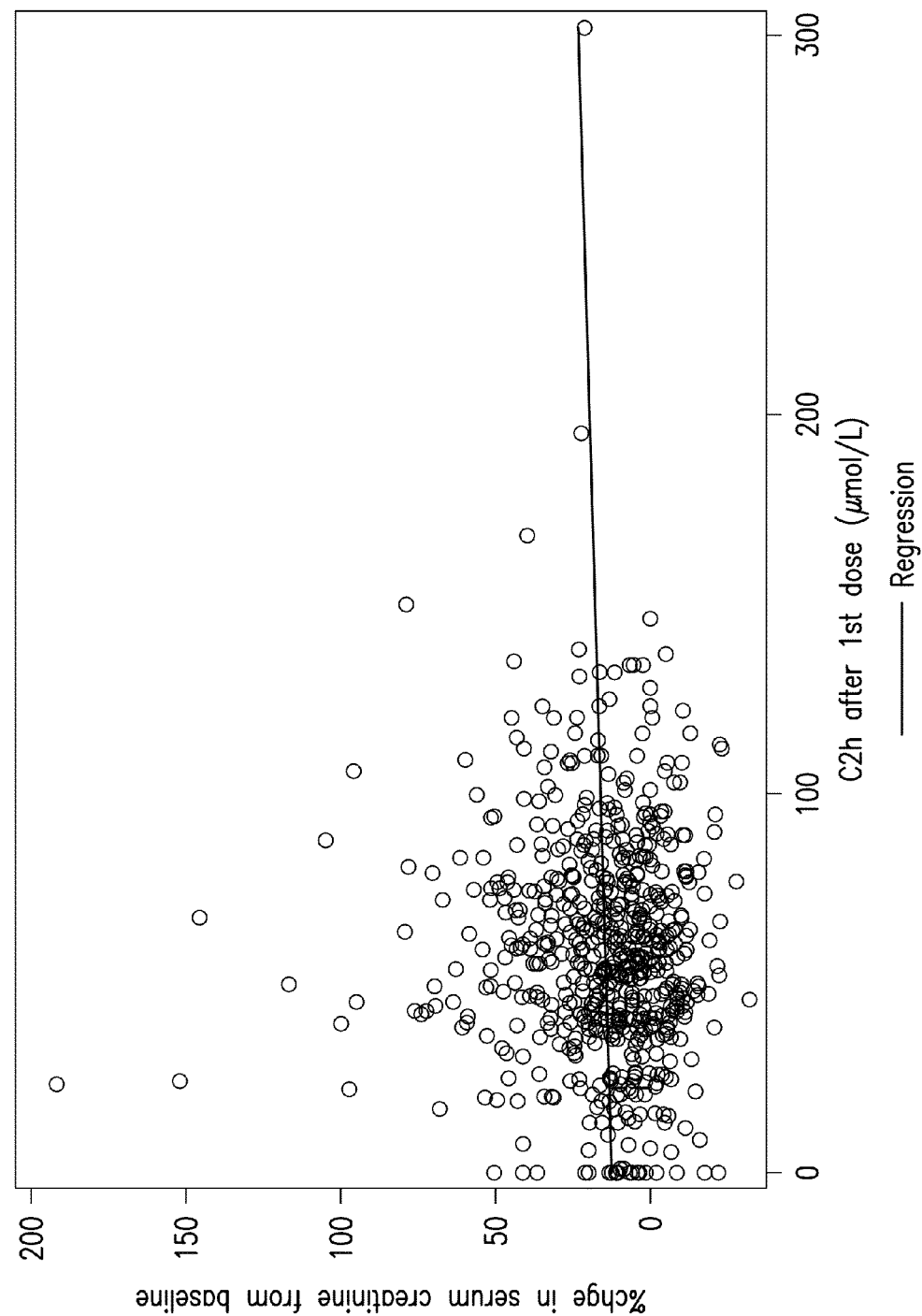
FIG. 11 summarizes a scatterplot of deferasirox C2h for the invented formulation on Day 1 versus percent change from baseline in serum creatinine at Week 4.

Day 1 C2h values did not predict the extent of creatinine changes at week 4 (N=682): the slope of the linear regression between Day 1 C2h and percent change in serum creatinine at week 4 was 0.03 (−0.01, 0.08), with a p-value of 0.22, and R-square<0.01, as summarized in FIG. 11.

There was no statistical difference in the rate of serum creatinine increases (either >33% over baseline, or >33% over baseline and >ULN) between patients whose C2h value was below the median (56.5 μmol/L in this analysis) and those whose C2h value was at or above the median, based on the Chi-square test in a population exposed to a dose of approximately 20 mg/kg (N=528; Table 6). A similar analysis was performed considering another classification for Day 1 C2h using quartiles (<Q1; Q1-<median; median-<Q3; ≥Q3) and results led to the same conclusion.

TABLE 6

Statistical analysis of C2h on day 1 versus notable serum creatinine values at week 4 (dose range 17.5-22.5 mg/kg) for deferasirox formulation

|  | Day 1 C2h < median (N = 264); % (N) | Day 1 C2h ≥ median (N = 264); % (N) | Chi-square test p-value |
|---|---|---|---|
| SCr increase >33% from baseline at week 4 | 14.39% (38) | 18.56% (49) | 0.197 (NS) |
| SCr increase >33% from baseline and >ULN at week 4 | 5.68% (15) | 7.58% (20) | 0.382 (NS) |

A covariate analysis by an ordinal logistic regression model was performed to further elucidate the impact of each PK parameter on renal function, as summarized in Table 7. $C_{trough}$ had a strong impact on creatinine clearance (CRCL) change in categories, but C2h had almost no impact (p-value=0.994), after adjusting for Ctrough. A C2h increase by 1.3-fold would provide an odds ratio (OR) of 0.999 (0.872; 1.146). This suggests that the new invented deferasirox formulations (comparable AUC but higher $C_{max}$ than the current marketed formulation) would result in a comparable effect on renal function.

All analyses summarized in this section will be described in full detail in the registration dossiers for the FCT and the granules.

REFERENCES

Cappellini M D, Bejaoui M. Agaoglu L, et al (2007). Prospective evaluation of patient-reported outcomes during treatment with deferasirox or deferoxamine for iron overload in patients with beta-thalassemia. Clin Ther 29.909-917.

Chirnomas D. Smith A L. Braunstein J et al (2009): Deferasirox pharmacokinetics in patients with adequate versus inadequate response. Blood 114(19): 4009-13

Mednick L M, Braunstein J. Neufeld E (2010) Oral chelation: Should it be used with young children. Pediatr Blood Cancer 55:603-605

Osborne R H, Lourenco R D, Dalton A. et al (2007). Quality of life related to oral versus subcutaneous iron chelation: A time trade-off study. Value Health 10:451-456.

It is understood that while the present invention has been described in conjunction with the detailed description thereof that the foregoing description is intended to illustrate and not limit the scope of the invention, which is defined by the scope of the following claims. Other aspects, advantages and modifications are within the scope of the claims.

What is claimed:

1. A tablet for oral administration consisting of 90 mg deferasirox;
   53.61 mg microcrystalline cellulose;
   3.65 mg poly vinyl pyrrolidone K-30;
   11.34 mg crospovidone;
   0.16 mg poloxamer;
   0.81 mg fumed silica;
   2.43 mg magnesium stearate; and
   4.86 mg seal-coat.

2. A tablet for oral administration consisting of 180 mg deferasirox;
   107.23 mg microcrystalline cellulose;
   7.29 mg poly vinyl pyrrolidone K-30;
   22.68 mg crospovidone;
   0.32 mg poloxamer;
   1.62 mg fumed silica;
   4.86 mg magnesium stearate; and
   9.72 mg seal-coat.

3. A tablet for oral administration consisting of 360 mg deferasirox;
   215.45 mg microcrystalline cellulose;
   14.58 mg poly vinyl pyrrolidone K-30;

TABLE 7

Summary results of ordinal logistic regression model analysis based on week 12 data

| Parameter | Estimate | Std error | Pr > ChiSq | OR* for a 2-fold increase in PK parameter (95% CI) | OR* for a 30% increase in PK parameter (95% CI) |
|---|---|---|---|---|---|
| Log(baseline creatinine clearance) | −10.3474 | 0.6405 | <0.0001 |  |  |
| Log(C2h) | −0.00203 | 0.2663 | 0.9939 | 0.999 (0.695, 1.434) | 0.999 (0.872; 1.146) |
| Log($C_{trough}$) | 0.9346 | 0.1653 | <0.0001 | 1.911 (1.527, 2.393) | 1.278 (1.174; 1.391) |

Response profile based on the following CrCl Categories (with ordered value):
1: 90 ml/min or more (N = 766);
2: 60 to <90 ml/min (N = 193);
3: 15 to <60 ml/min (N = 77);
*OR: Odds Ratio 45.36 mg crospovidone;
0.65 mg poloxamer;
3.24 mg fumed silica;
9.72 mg magnesium stearate; and
19.44 mg seal-coat.

\* \* \* \* \*